US012678335B2

(12) United States Patent
Stojanov

(10) Patent No.: US 12,678,335 B2
(45) Date of Patent: Jul. 14, 2026

(54) SURGICAL KNIFE WITH RETRACTABLE BLADE

(71) Applicant: Alcon Inc., Fribourg (CH)

(72) Inventor: Venjamin Stojanov, Dietlikon (CH)

(73) Assignee: Alcon Inc., Fribourg (CH)

( * ) Notice: Subject to any disclaimer, the term of this patent is extended or adjusted under 35 U.S.C. 154(b) by 40 days.

(21) Appl. No.: 18/737,068

(22) Filed: Jun. 7, 2024

(65) Prior Publication Data

US 2024/0423842 A1 Dec. 26, 2024

Related U.S. Application Data

(60) Provisional application No. 63/509,574, filed on Jun. 22, 2023.

(51) Int. Cl.
 A61F 11/20 (2022.01)
 A61B 17/3209 (2006.01)
(52) U.S. Cl.
 CPC ........... A61F 11/20 (2022.01); A61B 17/3209 (2013.01); A61B 2217/005 (2013.01)
(58) Field of Classification Search
 CPC ........ A61F 11/20; A61F 9/0133; A61F 9/013; A61F 9/00763; A61F 9/00754; A61F 9/00736; A61F 9/00745; A61F 9/007; A61F 11/202; A61B 17/3209; A61B 2217/005; A61B 2017/00787; A61B 17/320708; A61B 2017/32113; A61B 2090/08021; A61B 17/320016; A61B 17/32002; A61B 17/3211; A61B 17/320783; A61B 17/32; A61B 2217/007; A61B 2018/1412; A61B 2018/1455;

A61B 17/32053; A61B 17/320725; A61B 2018/00601; A61B 2017/320052; A61B 2017/0046; A61B 17/3417; A61B 17/3213; A61B 17/3207; A61B 2017/320028; A61B 17/32075; A61B 17/32093; A61B 2017/32004; A61B 2017/00261; A61B 17/3496; A61B 17/3205; A61B 2017/320791;
(Continued)

(56) References Cited

U.S. PATENT DOCUMENTS

| | | | | |
|---|---|---|---|---|
| 4,674,500 A | * | 6/1987 | DeSatnick | A61B 17/3211 |
| | | | | 30/286 |
| 4,885,004 A | | 12/1989 | Pao | |

(Continued)

OTHER PUBLICATIONS

Alcon Surgical Retina Product Catalog, 2019 (36 pages).

*Primary Examiner* — Tan-Uyen T Ho
*Assistant Examiner* — Bridget E. Rabaglia

(57) ABSTRACT

A surgical knife for ear surgery includes a handle comprising a control mechanism and a shaft coupled to and extending distally from the distal end of the handle. A rod disposed within the shaft comprising a distal end and a proximal end opposite the distal end, wherein the proximal end of the rod is coupled to the control mechanism and wherein the rod is configured to translate along a longitudinal axis of the shaft upon actuation of the control mechanism. The surgical knife further includes a straight knife coupled to the distal end of the rod, wherein translation of the rod causes the straight knife to extend or retract out of the distal end of the shaft. The surgical knife further includes a round knife attached to the distal end of the shaft.

12 Claims, 4 Drawing Sheets

(58) Field of Classification Search
    CPC .. A61B 2017/320008; A61B 17/00234; A61B
        2018/00404; A61B 10/0233; A61B 17/34;
                                A61B 2017/320024
    USPC ....... 606/170, 109, 167, 180, 171, 185, 160,
            606/45, 196, 159, 161, 166, 172; 604/22,
            604/35; 600/104, 566, 570, 564, 200,
                                            600/471
    See application file for complete search history.

(56)                    References Cited

U.S. PATENT DOCUMENTS

| | | | |
|---|---|---|---|
| 5,258,002 A | 11/1993 | Jeffers et al. | |
| 5,876,416 A | 3/1999 | Hill | |
| 5,961,441 A | 10/1999 | Plumb | |
| 6,855,156 B2 | 2/2005 | Etter | |
| 6,908,476 B2 | 6/2005 | Jud | |
| 9,615,973 B1 | 4/2017 | Frederick | |
| 10,524,818 B2 | 1/2020 | Liu | |
| 11,413,191 B2 | 8/2022 | Watanabe | |
| 11,467,386 B2 | 10/2022 | De Juan | |
| 11,490,915 B2 | 11/2022 | Abt | |
| 11,752,036 B2 | 9/2023 | Grueebler | |
| 12,029,687 B2 | 7/2024 | Kahook | |
| 2004/0181248 A1* | 9/2004 | Josephson | A61F 11/20 606/167 |
| 2008/0249552 A1 | 10/2008 | Eliachar | |
| 2009/0204135 A1 | 8/2009 | Cote | |
| 2010/0298853 A1 | 11/2010 | Slater | |
| 2016/0143660 A1* | 5/2016 | Castro | A61B 17/32 606/170 |
| 2016/0235430 A1 | 8/2016 | Huffenus | |
| 2016/0346511 A1 | 12/2016 | Cohen | |
| 2019/0314089 A1* | 10/2019 | Shameli | A61B 34/20 |
| 2021/0228411 A1 | 7/2021 | De Juan | |
| 2021/0275206 A1 | 9/2021 | Anderson | |
| 2022/0362057 A1 | 11/2022 | Charles | |

* cited by examiner

SURGICAL KNIFE WITH RETRACTABLE BLADE

BACKGROUND

The human ear is subject to a variety of disorders including, but not limited to, acoustic neuroma, acoustic trauma, balance disorders including vertigo, barotrauma, cholesteatoma, exostosis, hearing loss, labyrinthitis, Ménière's disease, ossicular chain dislocation, outer ear infections, middle ear infections, vestibular neuritis, vestibular schwannomaotosclerosis, schwannoma, tinnitus, and tympanic membrane perforations, to provide a few examples.

Access to the ear canal, tympanic membrane, middle ear, and inner ear has historically been challenging due to angulation and/or small size of such structures, the delicateness of various ear tissues, and the relatively large size of available surgical instruments. Moreover, instruments specifically designed for various otologic (ear) procedures are lacking.

Therefore, there is a need for improved methods, devices, and surgical instruments for otologic procedures.

SUMMARY

Aspects of the present disclosure relate to instruments for otologic (ear) procedures, and more particularly, to cutting instruments for otologic surgical procedures.

In certain embodiments, a surgical knife for otologic procedures is provided. The surgical knife comprises a handle and a shaft coupled to a distal end of the handle. A movable rod is at least partially disposed within the shaft and coupled, at a proximal end thereof, to a control mechanism of the handle. A round blade is fixedly coupled to a distal end of the shaft, and a straight blade is fixedly coupled to a distal end of the rod. Upon actuation of the control mechanism of the handle, the rod is configured to translate along a major longitudinal axis of the shaft, such that the translation of the rod causes the straight knife to extend or retract from the distal end of the shaft.

BRIEF DESCRIPTION OF THE DRAWINGS

The drawings described herein are for illustrative purposes only, are schematic in nature, and are intended to be exemplary rather than to limit the scope of the disclosure.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

Aspects of the present disclosure relate to instruments for otologic (car) procedures, and more particularly, to cutting instruments for otologic surgical procedures.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body. Further, as described herein, a major axis of a component refers to an axis or line passing through a center point of a longitudinal or lateral cross-section of the component.

A surgeon may use several surgical instruments for the successful completion of an otologic surgical procedure. Two of such instruments include a round knife and a straight knife. For example, during middle ear surgeries in which the tiny, delicate structures within or adjacent to the middle ear cavity are operated on, a tympanomcatal flap may be formed in the external auditory canal (EAC) using both a round knife and a straight knife. Together with the tympanic annulus, the tympanomeatal flap may be elevated to provide a surgeon with access to the middle ear space. Examples of procedures during which a tympanomcatal flap may be formed include tympanoplastics, ossiculoplastics, and stapes surgeries, as well as other types of postauricular, transcanal, or endaural middle ear surgical procedures, to name a few.

Figures 1A, 1B, 1C, 1D, 1E, 1F:
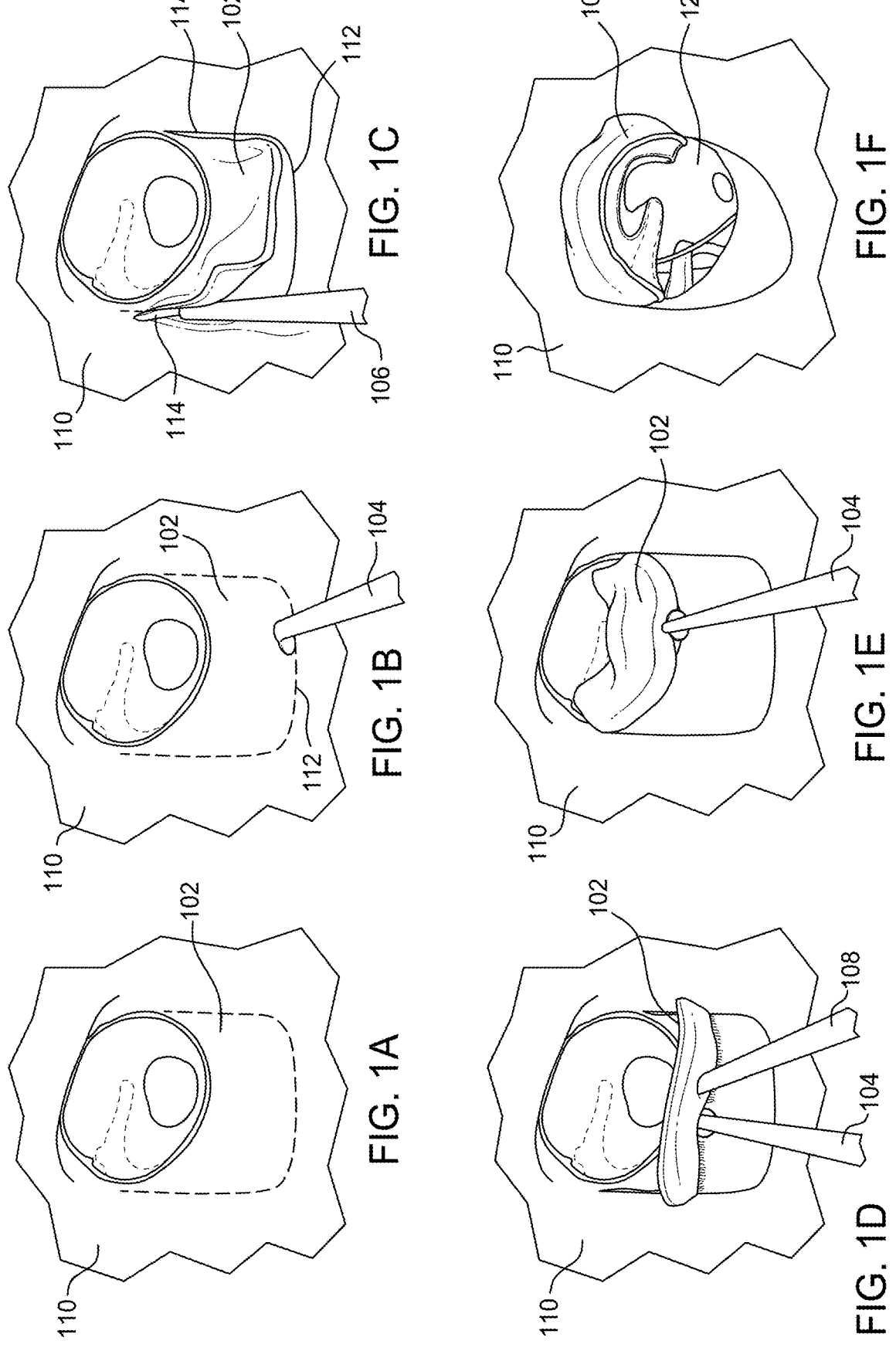
FIG. 1A-1F illustrate various operations of an otologic procedure wherein a tympanomeatal flap is formed using a round knife and a separate straight knife.

FIGS. 1A-1F illustrate exemplary stepwise operations in the formation of a tympanomcatal flap 102 during a postauricular procedure utilizing a round knife and a separate straight knife. Generally, a series of incisions are made at various angles to create the tympanomeatal flap 102, which may thereafter be lifted/folded to gain access to the anatomy beneath. FIG. 1A illustrates an incision outline of the tympanomeatal flap 102 to be cut from tympanomeatal tissue 110. In FIG. 1B, a round knife 104 is utilized to create a first, "horizontal" incision 112 that is substantially perpendicular to the longitudinal axis of the EAC. In certain examples, the round knife 104 may be used to "crush" the tympanomeatal tissue 110 to reduce bleeding and maintain a smoothly cut incision 112. Thereafter, in FIG. 1C, a straight knife 106 is utilized to create two "vertical" incisions 114 that are substantially parallel to the longitudinal axis of the EAC and intersect with the incision 112. The combination of the two "vertical" incisions 114 and the "horizontal" incision 112 form the tympanomeatal flap 102. In certain examples, prior to forming the incisions 114, the surgeon may "tunnel" superiorly under the tympanomcatal tissue 110 where the incisions 114 are to be made to facilitate smooth cutting. In FIGS. 1D-1E, the round knife 104 and a separate auxiliary tool, such as a suction tube 108, may be utilized to manually elevate/fold the tympanomeatal flap 102 in the EAC toward the annulus. Finally, in FIG. 1F, the annulus along with the tympanomeatal flap 102 is elevated and the middle ear space 120 is exposed to provide the surgeon access to the middle ear space 120.

The utilization of multiple different instruments during an otologic procedure, such as during the formation of the tympanomcatal flap 102 in FIGS. 1A-1F, and their repeated insertion and/or removal into the ear may increase the risk of unwanted trauma to surrounding ear tissues, and/or increase the time needed for surgery. Further, the repeated exchange of instruments may decrease the efficiency of the otologic procedure and increase inconvenience for the surgeon.

To address at least some of the aforementioned concerns, the present disclosure provides an otologic surgical knife having both a round blade and a straight blade to facilitate the formation of different types of incisions with a single instrument, thereby reducing the number of instruments needed during certain otologic procedures. Such a surgical knife may be utilized, for example, to create and elevate and/or fold a tympanomeatal flap in the external auditory canal for access to the middle ear space. Because the surgical knife comprises both a round blade and a straight blade, a surgeon may maintain and utilize the same knife to make various types of incisions in the external auditory canal. Thus, in certain examples, the surgical knife described herein reduces the number of instrument exchanges during an otologic procedure, which in turn increases the case of use and convenience for the surgeon, improves procedural efficiency, reduces overall time of the surgery, and reduces the risk of trauma to the patient's ear tissues.

Figures 2A, 2B, 2C, 2D:
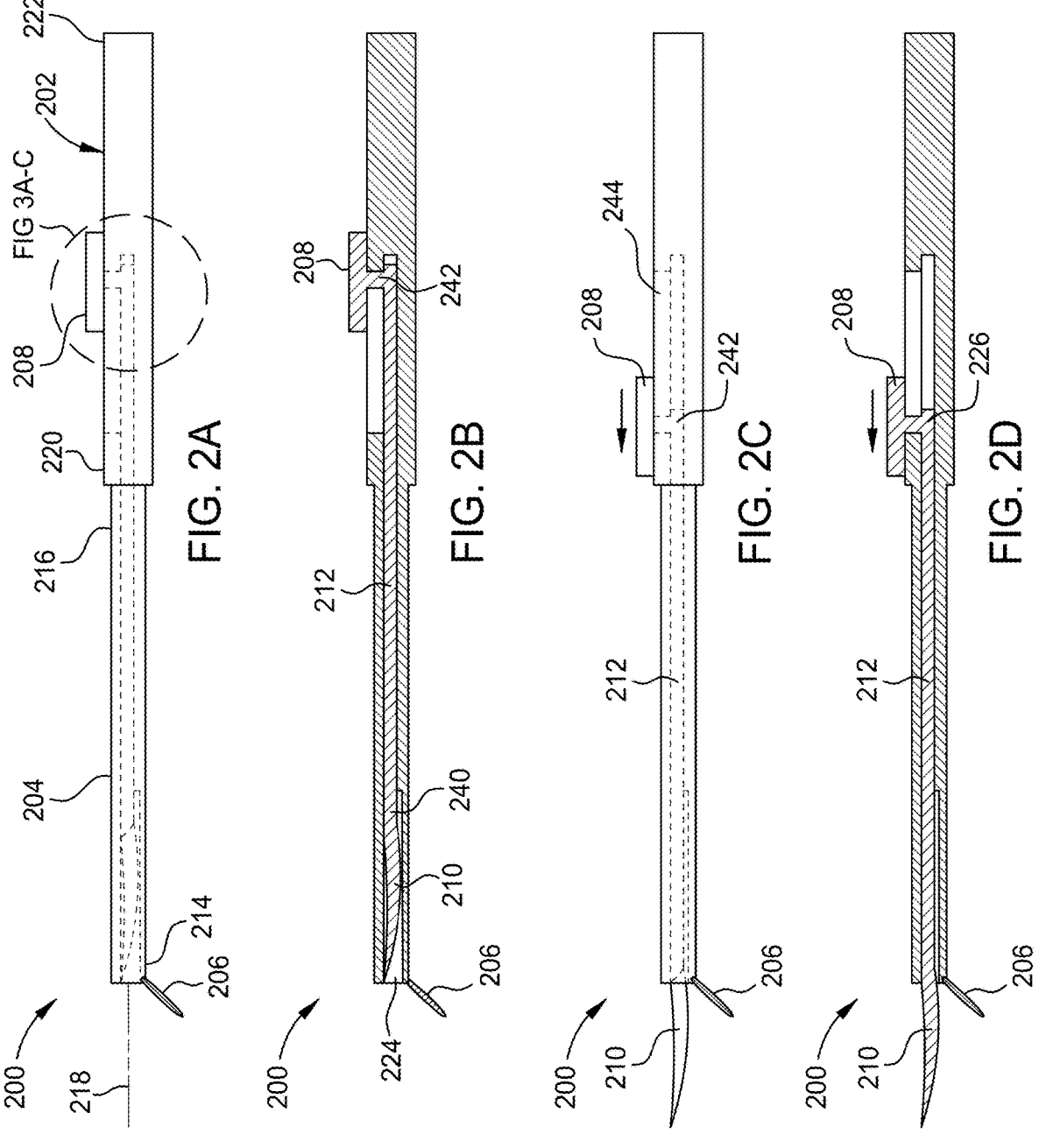
FIG. 2A illustrates a schematic side view of a surgical knife having a fixed round blade and an actuatable straight blade, in a retracted position, according to embodiments described herein.
FIG. 2B illustrates a cross-sectional side view of the surgical knife of FIG. 2A in a retracted position, according to embodiments described herein.
FIG. 2C illustrates a schematic side view of the surgical knife of FIG. 2A with the straight blade in an extended position, according to embodiments described herein.
FIG. 2D illustrates a cross-sectional side view of the surgical knife of FIG. 2A in an extended position, according to embodiments described herein.

FIGS. 2A-2B illustrate a schematic side view and a cross-sectional side view, respectively, of an exemplary surgical knife 200 in a "retracted" position, according to embodiments described herein. For clarity, FIGS. 2A-2B are herein described together.

As shown, the surgical knife 200 generally includes a handle 202 and a shaft 204 coupled to and extending distally from a distal end 220 of the handle 202. In certain embodiments, the shaft 204 is removably coupled to the handle 202. In certain embodiments, the shaft 204 is fixedly coupled to the handle 202.

The handle 202 further includes a proximal end 222 opposite the distal end 220. In certain embodiments, handle 202 is a hand piece having an outer surface configured to be held by a user, e.g., a surgeon. As such, the outer surface of the handle 202 may be ergonomically contoured for holding by the user. In certain embodiments, the outer surface of the handle 202 may be textured or have one or more gripping features formed thereon, such as one or more grooves, ridges, and/or other patterns. Generally, the handle 202 may be made from any material(s) commonly used for such instruments and suitable for otologic surgery. For example, the handle 202 may be formed of lightweight aluminum, stainless steel (or other metal alloys), a thermoplastic polymer, and/or other suitable material(s). In certain embodiments, the handle 202 may be configured to be sterilized and used in more than one surgical procedure. In other embodiments, the handle 202 is configured for a single use.

The shaft 204 generally comprises an elongated tubular member having a proximal end 216 coupled to the handle 202 and a distal end 214 opposite the proximal end 216. In certain embodiments, the shaft 204 has a cylindrical shape. In certain embodiments, the shaft 204 has a polygonal tubular shape. In certain embodiments, the shaft 204 is substantially linear. In certain embodiments, the shaft 204 comprises a curvature. However, any suitable shapes and/or morphologies are contemplated for the shaft 204.

Similar to the handle 202, the shaft 204 may be made from any material(s) commonly used for such instruments and suitable for otologic surgery. For example, the shaft 204 may be formed of lightweight aluminum, stainless steel (or other metal alloys), a thermoplastic polymer, and/or other suitable material(s). In certain embodiments, the shaft 204 is made from the same material as the handle 202. In certain embodiments, the shaft 204 is made from a different material than the handle 202. In certain embodiments, the shaft 204 may be configured to be sterilized and used in more than one surgical procedure. In other embodiments, the shaft 204 is configured for a single use.

A round blade 206 is coupled to the distal end 214 of the shaft 204. In certain embodiments, the round blade 206 is fixedly coupled to the distal end 214 of the shaft 204 at a non-zero angle relative to a major longitudinal axis 218 of the shaft 204. The non-zero angle may be between about 30 degrees to about 70 degrees relative the longitudinal axis 218 of the shaft 204, such as an angle between about 40 degrees to about 60 degrees relative to the longitudinal axis 218.

In certain embodiments, the angle of the round blade 206 may be adjusted via plastic deformation of the shaft 204, thereby creating an adjustable round blade 206. For example, the distal end 214 of the shaft 204 may be formed of a flexible thermoplastic material such that the round blade 206, coupled to the distal end 214 of the shaft 204, may be bent to accommodate the surgeon's preferred angle. Prior to bending, the round blade 206 may be positioned at an angle of 0 degrees relative to the longitudinal axis 218 of the shaft 204. The surgeon may then manually bend the round blade 206 to the desired angle relative to the longitudinal axis 218, or use an additional surgical instrument (e.g., forceps) to bend the round blade 206. Examples of suitable thermoplastics include polypropylene, polyethylene, polyvinylchloride, polystyrene, polyethylenetheraphthalate, polycarbonate, thermoplastic urethanes, and the like.

As shown in FIG. 2B, a channel 224 extends from the handle 202 to the distal end 214 of the shaft 204, and comprises a rod 212 at least partially disposed therein. A straight blade 210 rigidly couples to a distal end 240 of the rod 212. In the retracted position, the straight blade 210 is substantially sheathed within the channel 224 of the shaft 204. Meanwhile, a proximal end 242 of the rod 212 is coupled to a control member 208 within the handle 202. Actuation of the control member 208 by the user causes the rod 212 to translate longitudinally within the channel 224 between the retracted position and an "extended" position, thereby facilitating egress/ingress of the straight blade 210 from the distal end 214 of the shaft 204. In certain embodiments, the rod 212 may be configured to translate substantially along, or substantially parallel to, the longitudinal axis 218 of the shaft 204.

In certain embodiments as shown in FIGS. 2A-2B, the longitudinal axis 218 of the shaft 204 is parallel or collinear with a major longitudinal axis of the handle. However, in other embodiments, to improve visibility for the surgeon, the longitudinal axis 218 of the shaft 204 may be disposed at a non-zero angle relative to the major longitudinal axis of the handle 202. In certain embodiments, the shaft 204 may be coupled to the handle 202 at an angle between about 0 degrees and about 90 degrees relative to the longitudinal axis 218 of the shaft 204 and/or the major longitudinal axis of the handle 202. For example, in certain embodiments, the shaft 204 may be coupled to the handle 202 at an angle between about 30 degrees and about 60 degrees relative to the major longitudinal axis of the handle 202, such as an angle of about 45 degrees. Further, in certain embodiments, the shaft 204 may be rotatable relative to the handle 202. In certain embodiments, the shaft 204 may have a maximum diameter between about 1 millimeter to about 3 millimeters to further improve visibility and prevent the shaft 204 from blocking the surgeon's view of, e.g., the middle ear space during a procedure.

FIGS. 2C-2D illustrate a schematic side view and a cross-sectional view, respectively, of the exemplary surgical knife 200 in the extended position, according to embodiments described herein.

As shown in FIGS. 2C-2D, in the extended position, at least a portion of the straight blade 210 extends distally beyond the distal end 214 of the shaft 204. In certain embodiments, an entire length L of the straight blade 210 may be distally extended beyond the distal end 214 of the shaft 204 in the extended position.

To extend the straight blade 210 distally from the distal end 214 of the shaft 204, the user may actuate the control member 208 that is operably coupled to the handle 202 and the proximal end 216 of the rod 212. In certain embodiments, the control member 208 is fixedly attached at the proximal end 242 of the rod 212 within the shaft 204. In such embodiments, the control member 208 may comprise a sliding mechanism, such as a sliding button, wherein the sliding button is positioned at the proximal end of a trough 244 when the straight blade 210 is retracted into the shaft 204. The sliding button may be manually translated by a user to a distal end of the trough 244 to move the straight blade 210 to the extended position. In certain other embodiments, the control member 208 may comprise a leadscrew mechanism, a squeezing mechanism, or an electromotor controlled by a button or switch on the handle 202 or another user input device, such as a foot pedal.

The combined functionalities of the surgical knife 200 facilitate safer and more efficient performance of otologic procedures. As an illustrative example, the surgical knife 200 may be used to efficiently form a tympanomeatal flap and elevate the tympanomeatal flap during a postauricular middle ear surgery. For example, a surgeon may first insert the surgical knife 200 into the external auditory canal (EAC) in a "retracted" position, wherein the straight blade 210 is disposed within the shaft 204. The surgeon may then use the round blade 206 to create a "horizontal" incision in the tympanomeatal tissue, as described in FIG. 1B above, that is substantially perpendicular to the longitudinal axis of the EAC. Thereafter, the surgeon may, via manual manipulation of the control member 208, transition the surgical knife 200 to the "extended" position such that at least a portion of the straight blade 210 extends from the shaft 204.

Before or after transitioning to the extended position, the surgeon may rotate the handle 202 at a desired rotational angle, such as a rotational angle of about 90 degrees, so that the straight blade 210 is appropriately oriented (when extended) to create two "vertical" incisions in the tympanomeatal tissue that are substantially parallel to the longitudinal axis of the EAC, as described in FIG. 1C above. The two "vertical" incisions may be cut with the extended straight blade 210 such that they intersect with the "horizontal" incision. Thereafter, the surgeon may use the control member 208 to transition the surgical knife 200 back to the retracted position and sheathe the straight blade 210 in the shaft 204. The surgeon may then again rotate the handle 202 and use the round blade 206 to lift the tympanomeatal flap formed by the horizontal and vertical incisions, thereby allowing the surgeon access to the middle ear space.

Figure 3A:
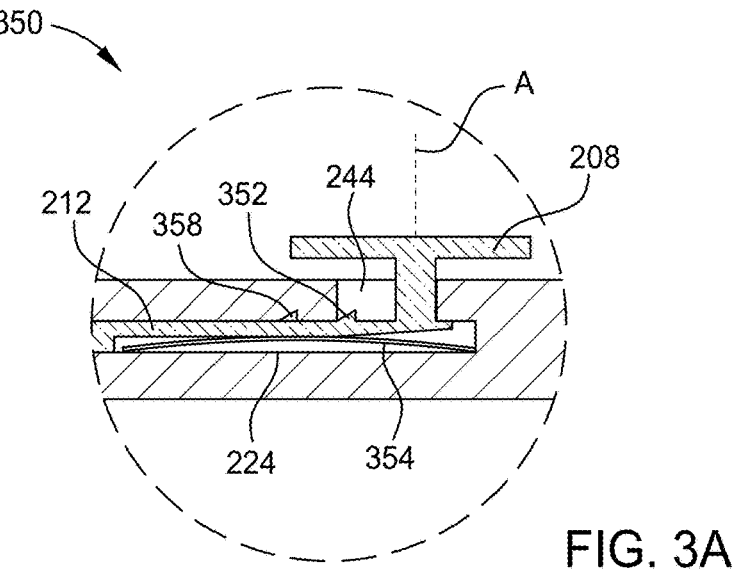
FIGS. 3A-3C illustrate detailed cross-sectional side views of an exemplary locking mechanism, according to embodiments described herein.
Figure 3B:
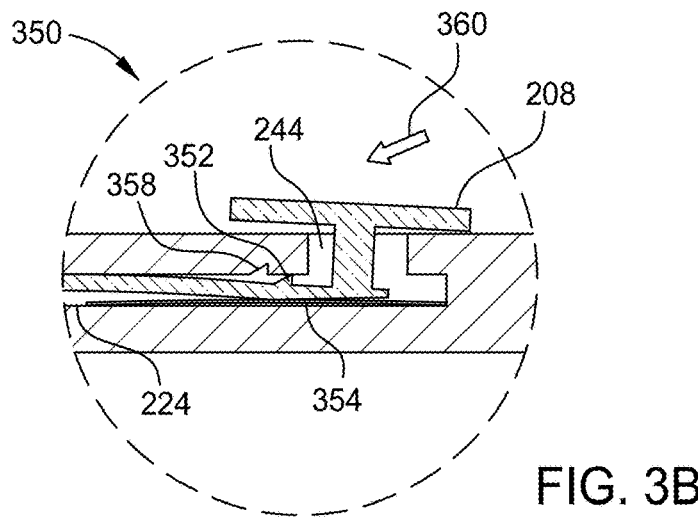
Figure 3C:
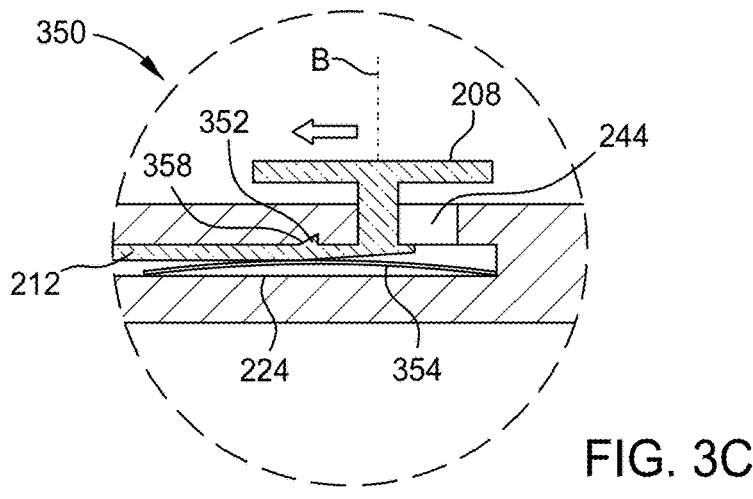

FIGS. 3A-3C illustrate detailed cross-sectional side views of an exemplary locking mechanism 350 for a control member of a surgical knife, according to embodiments described herein. In FIGS. 3A-3C, the control member 208 of surgical knife 200 is depicted for illustrative purposes. Generally, the control member 208 may be locked or maintained, via the locking mechanism 350, in at least a first preset position A and a second preset position B, wherein a straight blade operatively coupled to the control member 208 (e.g., the straight blade 210) is disposed external to a shaft (e.g., the shaft 204) and outside the shaft, respectively. However, a locking mechanism 350 with three or more preset positions is also contemplated. Even further, in certain embodiments, the locking mechanism 350 may have continuous positioning, or be without fixed preset positions, such that the locking mechanism 350 may be locked or maintained at any point or increment along a range of positions. In such embodiments, the locking mechanism 350 may be secured in place by frictional forces between the control member 208 and the top of the channel 224 as caused by the biasing of the control member 208 by the spring 354.

Turning to FIG. 3A, the locking mechanism 350 comprises a spring-based locking mechanism having a spring 354 and one or more locking grooves 358 configured to mate with one or more protrusions 352 on the control member 208 (or the rod 212). Please note that other types of biasing members may also be used. In FIG. 3A, control member 208 is depicted as being held in the first preset position A, where the control member 208 is positioned at a proximal end of the trough 244 and the operatively coupled straight blade is sheathed within the shaft of the surgical knife. In this position, the spring 354, located at a bottom of the trough 244, presses the rod 212 against the top of the channel 224. This causes the one or more protrusions 352 of the control member 208, which are formed on an upper surface of the control member 208, to mate with the one or more locking grooves 358 formed on an upper surface of the channel 224, or, as shown in FIG. 3A, to abut an edge of the trough 244. This engagement secures the control member 208 and thus, the rod 212 and the straight blade coupled thereto, in place. When in this first position A, to laterally adjust the control member 208 and extend the straight blade from the shaft of the surgical knife, a user must apply a downward force against the control member 208, which disengages the protrusion(s) 352 from the locking groove(s) 358 or trough 244, prior to laterally moving the control member 208.

In FIG. 3B, a downward force 360 is applied by the user to the control member 208, causing the spring 354 to flatten and the protrusion(s) 352 to disengage from the locking groove(s) 358 and/or the edge of the trough 244. The user then manually laterally translates control member 208 towards the distal end of the trough 244, causing the rod 212 and operatively coupled straight blade to move distally.

Turning now to FIG. 3C, upon translation of the control mechanism 208 towards the distal end of the trough 244, the one or more protrusions 352 reengage with the one or more locking grooves 358 and/or the trough 244, as facilitated by the upward biasing provided by the spring 254. Accordingly, the reengagement holds the control member 208 in the second preset position B, wherein the straight blade is extended from the shaft of the surgical knife. To readjust the control member 208 from the second position B, the user may have to exert another downward force against the control member 208, and the spring 354 by association, to disengage the one or more protrusions 352 and enable lateral movement of the control member 208.

Figures 4A, 4B, 5:
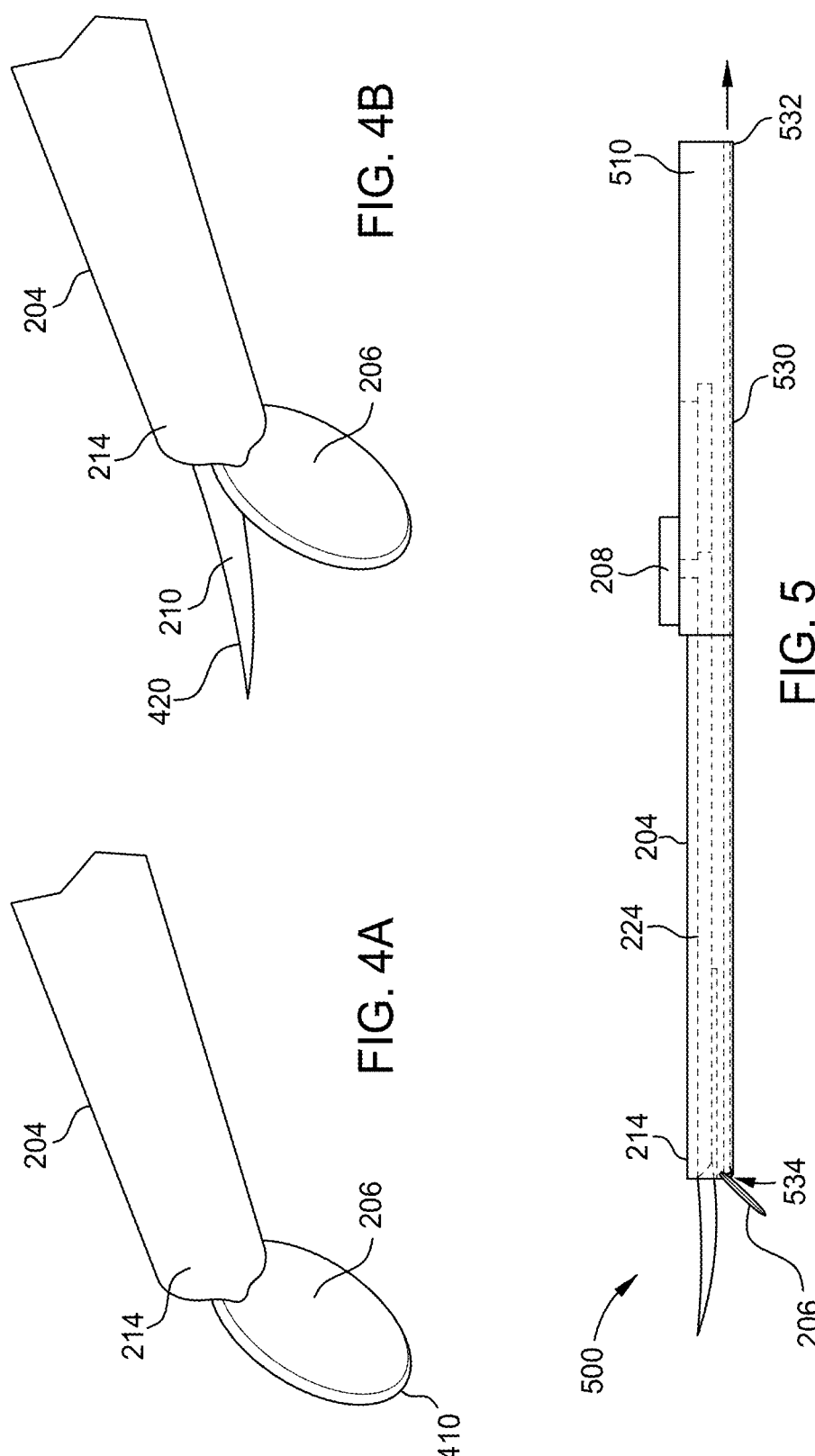
FIG. 4A-4B illustrate detailed perspective views of a round blade and straight blade, wherein the straight blade is in a retracted position and an extended position, respectively, according to embodiments described herein.
FIG. 5 illustrates a schematic side view of an exemplary surgical knife, in an extended position, according to embodiments described herein.

FIG. 4A-4B illustrate detailed perspective views of the round blade 206 of surgical knife 200 while the straight blade 210 is in a retracted position and an extended position, respectively, according to embodiments described herein.

As shown in FIG. 4A, the round blade 206 couples to the shaft 204 at the distal end 214. In certain embodiments, the round blade 206 comprises a disc-like blade with a rounded cutting edge 410. For example, the round blade 206 may have a substantially circular or oval disc-like geometry with the rounded cutting edge 410. However, other morphologies are also contemplated, such as a substantially quadrilateral (or polygonal) geometry with the rounded cutting edge 410 on one (or more) sides. In certain embodiments, the round blade 206 may comprise both sharp (cutting) and dull (non-cutting) edges. For example, in embodiments where the round blade 206 comprises a circular, disc-like shape, only a most distal one-third of a circumference of the round blade 206 may be sharpened to form the cutting edge 410 for creating incisions. Meanwhile, the remainder of the circumference of the round blade 206 may be dull to prevent unwanted cutting or trauma to ear tissues during use of the surgical knife 200.

In FIG. 4B, the straight blade 210 is disposed in the extended position, wherein at least a portion of the straight blade 210 protrudes form the distal end 214 of the shaft 204. As shown, the straight blade 210 comprises a cutting edge 420, which may be substantially linear (e.g., straight) or may have a slight convex or concave curvature. For example, in certain embodiments, the straight blade 210 may have sickle-like shape. Generally, the straight blade 210 may be oriented such that the cutting edge 420 of the straight blade 210 is directed away from the round blade 206. Accordingly, during use and in the extended position, the surgical knife 200 can be rotated to switch between the straight blade 210 and the round blade 206 without interference from the round blade 206.

FIG. 5 illustrates a schematic side view of another exemplary surgical knife 500, in an extended position as in FIG. 2C, according to certain embodiments herein. The surgical knife 500 is substantially similar to the surgical knife 200, but further includes a suction tube 530 through which a vacuum pressure may be applied for clearing blood and/or debris during an otologic procedure and/or for increasing traction against otologic tissues being manipulated by the surgical knife 500. For clarity, features of the surgical knife 500 similar to those of surgical knife 200 are labelled with the same reference numerals.

As shown, the suction tube 530 extends through the handle 202, through the shaft 204, and to the distal end 214 of the shaft 204. The suction tube 530 is fluidly coupled to a distal port 534 at the distal end 214 of the shaft 204, and further to a proximal port 532 formed in the handle 202. In certain embodiments, the proximal port 532 is formed in a proximal end 510 of the handle 202. The proximal port 532 generally comprises an opening configured to be fluidically coupled with a vacuum source, such as vacuum source of a surgical console, via flexible tubing (or other suitable connector) for supplying vacuum pressure to the suction tube 530 and thus, the distal port 534. Meanwhile, the distal port 534 comprises an opening disposed at any suitable location at the distal end 214 for applying the supplied vacuum pressure to external blood, debris, and/or otologic tissues to "suck" them into or against the distal port 534. In certain embodiments, the distal port 534 is disposed below the round blade 206, or on a side of the round blade 206 opposite the channel 224.

As mentioned above, vacuum suction through the distal port 534 may be used during otologic procedures to clear blood, and/or debris from a surgeon's field of view, and/or to suction ear tissues against the distal port 534 to facilitate easier manipulation thereof. For example, when the round blade 206 is utilized to push/lift the tympanomeatal flap during a postauricular middle ear surgery, a vacuum source fluidly coupled to the suction tube 530 may be activated to provide a vacuum pressure through the distal port 534 and aspirate/clear blood, debris, and secretions from the middle ear cavity, and/or the EAC, for better visualization of ear structures by the surgeon. Alternatively, vacuum pressure may be provided through the distal port 534 to assist the surgeon in manipulating (e.g. lifting) the tympanomeatal flap. In such examples, the vacuum pressure generated by the vacuum source through proximal port 532 may be small enough to not damage the tympanomeatal flap and/or other ear tissues, but great enough to suction the tympanomeatal flap and elevate it with movement of the round blade 206.

In summary, embodiments of the present disclosure provide an otologic surgical knife having both a round blade and a straight blade to facilitate the formation of different types of incisions with a single instrument, thereby reducing the number of instruments needed during certain otologic procedures. Such a surgical knife may be utilized, for example, to create and elevate/fold a tympanomeatal flap in the external auditory canal for access to the middle ear space. Because the surgical knife comprises both a round blade and a straight blade, a surgeon may maintain and utilize the same knife to make various types of incisions in the external auditory canal. Thus, in certain examples, the surgical knife described herein reduces the number of instrument exchanges during an otologic procedure, which in turn increases the case of use and convenience for the surgeon, improves procedural efficiency, and reduces the risk of trauma to the patient's ear tissues.

While the foregoing is directed to embodiments of the present disclosure, other and further embodiments of the disclosure may be devised without departing from the basic scope thereof, and the scope thereof is determined by the claims that follow.

EXAMPLE EMBODIMENTS

Embodiment 1: A surgical knife, comprising: a handle configured to be held by a user, the handle comprising a control member; a shaft comprising a distal end and a proximal end opposite the distal end, the proximal end coupled to the handle; a rod disposed within the shaft and comprising a distal end and a proximal end opposite the distal end, wherein the proximal end of the rod is coupled to the control member, and wherein the rod is configured to translate along a longitudinal axis of the shaft upon actuation of the control member; a straight blade coupled to the distal end of the rod, wherein translation of the rod along the longitudinal axis causes the blade to extend from or retract into the distal end of the shaft; and a round blade fixedly attached to the distal end of the shaft.

Embodiment 2: The surgical knife of Embodiment 1, wherein the proximal end of the shaft is removably coupled to the handle.

Embodiment 3: The surgical knife of Embodiment 1, wherein the proximal end of the shaft is fixedly coupled to the handle.

Embodiment 4: The surgical knife of Embodiment 1, wherein the round blade is disposed at an angle between about 30 and to about 70 degrees relative to the longitudinal axis of the shaft.

Embodiment 5: The surgical knife of Embodiment 4, wherein the round blade is disposed at an angle between about 40 and to about 60 degrees relative to the longitudinal axis of the shaft.

What is claimed is:

1. A surgical knife, comprising:

a handle configured to be held by a user, the handle comprising a control member;

a unitary shaft comprising a distal end and a proximal end opposite the distal end, the proximal end coupled to the handle;

a rod slidably disposed within a channel of the unitary shaft and comprising a distal end and a proximal end opposite the distal end, wherein the proximal end of the rod is coupled to the control member, and wherein the rod is configured to translate along a longitudinal axis of the unitary shaft upon actuation of the control member;

a straight blade coupled to the distal end of the rod, wherein translation of the rod causes the straight blade to extend from or retract into the distal end of the unitary shaft; and a round blade fixedly coupled to the distal end of the unitary shaft at a non-zero angle relative to the longitudinal axis of the unitary shaft;

wherein the straight blade retracts into the unitary shaft to which the round blade is fixedly coupled;

wherein the straight blade has a fixed rotational orientation within the unitary shaft relative to the round blade such that a cutting edge of the straight blade is directed away from the round blade thereby allowing the surgical knife to be rotated to switch between the straight blade and the round blade without interference.

2. The surgical knife of claim 1, wherein an angle of the round blade relative to the longitudinal axis of the unitary shaft is adjustable via plastic deformation.

3. The surgical knife of claim 2, wherein the round blade is formed of a flexible thermoplastic material.

4. The surgical knife of claim 1, wherein the round blade comprises a substantially circular or oval disc-like shape.

5. The surgical knife of claim 1, wherein the straight blade comprises a linear, concave, convex, or sickle-like shape.

6. The surgical knife of claim 1, wherein the handle further comprises a locking mechanism for securing the control member in at least a first preset position and a second preset position.

7. The surgical knife of claim 1, wherein the handle further comprises a locking mechanism with continuous positioning for securing the control member at any position along a range of positions.

8. The surgical knife of claim 6, wherein the locking mechanism comprises a spring-based locking mechanism, and wherein the control member is configured to be unlocked by application of a downward force against the control member.

9. The surgical knife of claim 1, further comprising:

a suction tube disposed within the unitary shaft, the suction tube in fluid communication with a distal port disposed at the distal end of the unitary shaft and a proximal port disposed in the handle, wherein the proximal port is configured to be operably coupled with a vacuum source to provide a vacuum pressure at the distal port.

10. The surgical knife of claim 1, wherein the handle further comprises a locking mechanism for securing the control member in at least a first preset position, the locking mechanism comprising a spring configured to bias the control member such that a protrusion on the control member engages a corresponding locking groove formed in the handle.

11. The surgical knife of claim 1, wherein the handle further comprises a locking mechanism for securing the control member, wherein the control member is configured to be unlocked from the locking mechanism by application of a force transverse to the longitudinal axis of the unitary shaft.

12. The surgical knife of claim 1, wherein the unitary shaft is rotatable relative to the handle.

* * * * *